United States Patent [19]

Ayalew

[11] 4,009,266
[45] Feb. 22, 1977

[54] METHOD OF TREATMENT OF NEMATODE PARASITE INFECTIONS IN DOMESTIC ANIMALS

[76] Inventor: Liyew Ayalew, 275 Seigneurial West, Apt. 10, St. Bruno, Quebec, Canada

[22] Filed: June 26, 1975

[21] Appl. No.: 590,781

[30] Foreign Application Priority Data

July 10, 1974 Canada ............................. 204497

[52] U.S. Cl. ............................. 424/177; 424/240; 424/247; 424/251; 424/263; 424/270; 424/346
[51] Int. Cl.² ................ A61K 37/32; A61K 37/24; A61K 31/56
[58] Field of Search .......... 424/247, 240, 177, 346, 424/251, 263

[56] References Cited
UNITED STATES PATENTS 2,971,885   2/1961   Luther et al. ...................... 424/240

OTHER PUBLICATIONS

Jones – Veterinary Pharmacology & Therapeutics – 3rd edit. (1965), p. 615.

Primary Examiner—Sam Rosen

[57] ABSTRACT

There is described herein a new method of treatment for the control of gastrointestinal nematode parasites in domestic animals, particularly sheep and cattle, and compositions therefor, which comprises administering, preferably at stabling time, successively or concurrently, a lactogenic substance and an anthelmintic agent.

7 Claims, No Drawings

METHOD OF TREATMENT OF NEMATODE PARASITE INFECTIONS IN DOMESTIC ANIMALS

BACKGROUND OF THE INVENTION

The present invention relates to a new method of treatment for the control of gastrointestinal nematode parasites in domestic animals and compositions therefor.

Gastroenteritis caused by gastrointestinal nematode parasites in domestic animals such as horses, swine, goats, cats, dogs and particularly in sheep and cattle, is one of the major disease problems faced by the breeders and considerable economic losses are incurred unless it is properly controlled. The control measures include the therapeutic and prophylactic uses of anthelmintic agents and appropriate pasture and barn managements. The principles of control are outlined by Blood and Henderson in "Veterinary Medicine", 3rd. Edition, London, Baillière, Tindall and Cassell, 1968, pp 583–585.

Many species of gastrointestinal nematode parasites, such as, for example, species of Haemonchus, Ostertagia, Trichostrongylus, Cooperia, Nematodirus, Chabertia or Oesophagostomum may cause gastroenteritis in sheep and cattle. In sheep *Haemonchus contortus* and species of Ostertagia are of particular importance and cattle *Ostertagia ostertagi* is the prime contributor to the disease. The clinical symptoms associated with the infections caused by these parasites as well documented in "Veterinary Medicine", cited above, pp 614–628.

Nematode parasites are dependent on the host for survival and for the maintenance of the species. Infections are acquired by the animal, while grazing, by the ingestion of infective larvae (third larval stage). These infective larvae undergo in the gastrointestinal tract of the host two additional stages of larval development (fourth and fifth larval stages) before reaching maturity. The adult nematodes then produce eggs which are excreted in the faeces. The eggs hatch and the resulting larvae (first larval stage) undergo two successive free-living developmental stages, namely second and the infective third larval stages, respectively. The transformation of eggs to the third larval stage requires 1 to 6 weeks depending on the climatic conditions of the field. In the summer an average of 2 to 3 weeks is necessary for the ingested infective larvae to develop into adult nematodes. For example, dependent on field conditions eggs of *Haemonchus contortus* will reach the infective stage in 1 to 6 weeks and once ingested these larvae will mature 2 to 3 weeks later. Some species of gastrointestinal nematodes, for example *Haemonchus contortus*, are prolific egg-producers and unless the infections are rapidly controlled they contribute to the death or the unthriftiness of the hosts and also they contribute to further contaminations of the pastures. Many anthelmintic agents presently commercially-available are effective against the adult forms of these gastrointestinal nematodes and some of them are also active against their normally developing larval stages.

Outbreaks of parasitic gastroenteritis during the summer are fairly predictable and they may be easily controlled by the administration of anthelmintics. However outbreaks of parasitic gastroenteritis in cattle and sheep are not restricted to the grazing season. There are many reports of sudden gastroenteritis during the winter and spring stabling periods even though the animals were not exposed to contamination for weeks and months, see for example E. F. Johnson et al. in Can. J. Comp. Med., Vol. 20, p. 203 (1956); W.B. Martin et al. in Vet. Rec., Vol. 69, p. 736 (1957); H.C. Gibbs in Can. Vet. J., Vol. 5, p. 8 (1964); H. J. Smith et al. in Can. Vet. J., Vol. 13, p. 114 (1972). More characteristic are the phenomena of the "spring-rise" and the Type II Ostertagiasis, respectively observed in sheep and cattle. These phenomena are well documented, see example L. Ayalew et al. in Can. J. Comp. Med., Vol. 37, p. 79 (1973); L. Ayalew et al. in Can. J. Comp. Med., Vol. 37, p. 356 (1973); H. C. Gibbs in Vet. Med. Rev., p. 160 (1967); J. Armour in Vet. Rec. Vol. 86, p. 184 (1970) and H. J. Smith et al., cited above. While Type II Ostertagiasis in cattle may take place anytime during winter and may affect yearlings and adults (see H. J. Smith et al, cited above), the spring-rise phenomenon in sheep is mainly observed in lactating ewes 3 to 13 weeks after lambing. It is characterized by a dramatic increase in the number of eggs excreted in the faeces in the spring. These eggs contaminate the pastures early in the spring and constitute a major source of infection for lambs (see L. Ayalew et al., cited above). Anthelmintic agents are effective against the worms responsible for the outbreaks of parasitic gastroenteritis in winter or spring. However, the detection of the infections is often too late to prevent damages to the animals and resulting economic losses.

There is at present considerable evidence indicating that infective larvae of gastrointestinal nematode parasites that are ingested from early fall to stabling time and through winter months do not mature with the expected 2–3 weeks but instead become dormant or inhibited in their development at the fourth larval stage for up to 9 months. It is the sudden and unexpected massive maturation of these dormant or inhibited larvae which is responsible for the spring-rise in sheep and for the outbreaks of Type II Ostertagiasis in cattle or other sudden outbursts of parasitic gastroentertitis during the stabling season (see for example L. Ayalew et al., H. C. Gibbs, H. J. Smith et al. and J. Armour, respectively cited above). The presence of dormant or inhibited larvae is virtually impossible to detect, the animals failing to show clinical signs of disease and the egg counts being very low. Furthermore there are no anthelmintic agents presently effective against dormant or inhibitive larvae (see J. Armour, cited above) and consequently there are no agents capable of preventing their eventual maturation and the subsequent outbreak of parasitic gastroenteritis.

Although many explanations have been advanced (see for example J. D. Dunsmore in Nature, Vol. 186, p. 966 (1960); Anderson et al. in Vet. Rec., Vol. 77, p. 1196 (1965); E. J. L. Soulsby in "Biology of Parasites", New York, Academic Press, 1966, pp. 257–276; J. F. Michel in Int. J. Parasitol, Vol. 1, p. 31 (1971); R. V. Brunsdon in N. Z. Vet. J. Vol. 20, p. 183 (1972) and N. M. Blitz et al. in Int. J. Parasitol., Vol. 2, p. 5 (1972), the precise triggering mechanisms for the induction of inhibition or for the maturation of inhibited larvae remain unknown.

DESCRIPTION OF THE INVENTION

I have now found that the administration in the fall, prior to stabling time, or during the winter months of a lactogenic substance prevents most of the third stage infective larvae of gastrointestinal nematode parasites which are ingested at that time of the year by the grazing animals, from becoming dormant or inhibited in their development at the fourth larval stage and allows these infective larvae to develop normally into the adult forms whereby the latter become susceptible to the action of anthelmintic agents. Consequently the administration, successively or concurrently, of a lactogenic substance and of an anthelmintic agent provides a new method of treatment for the control of gastrointestinal nematode parasites in domestic animals, particularly sheep and cattle.

Although the treatment may be given throughout the year, it is particularly advantageous to treat the animals in the fall, prior to stabling time, when the ingestion of inhibition-prone larvae by the grazing animals is maximal. In Northern United States and Canada stabling time extends from October–November until April–May. This treatment renders the animals practically parasite-free at the time of stabling, since the lactogenic substance prevents the larval inhibition of most of the infective larvae being ingested by the grazing animals, allows their normal development to the adult forms and renders the latter susceptible to the action of the anthelmintic agent, successively or concurrently administered. As a consequence, this new method of treatment is also useful for the prevention of the sudden and unexpected outbreaks of parasitic gastroenteritis during the winter months and more particularly the occurrence of the "spring rise" phenomenon in sheep or Type II Ostertagiasis in cattle. As a further consequence this new method of treatment is also useful in preventing the contamination of the pastures during the following year.

Many agents, such as for example, prolactin, somatotropin, adrenal corticoid hormones or estrogens, are capable of initiating lactation (see, for instance, G. H. Schmidt in "Biology of Lactation", San Francisco, W. H. Freeman and Co. 1971, pp 94–97). Although these substances, as well as any agent capable of stimulating the release of prolactin, may be used as the lactogenic substance to prevent the third stage infective larvae of gastrointestinal nematode parasites from becoming dormant or inhibited in their development at the fourth larval stage, the preferred lactogenic substances are estrogens, more particularly diethylstilbestrol, estrone, estradiol, estradiol 3,17-diacylates such as for example estradiol 3,17-dipropionate or estradiol 3,17-dibenzoate, ethynylestradiol or mestranol. Concerning the anthelmintic agent which is administered concurrently or successively with the lactogenic substance, any anthelmintic agents, effective against the adult forms of the gastrointestinal nematode parasites responsible for parasitic gastroenteritis in domestic animals, particularly sheep and cattle, may be used. The preferred anthelmintic agents are phenothiazine, thiabendazole, cambendazole, mebendazole, tetramisole, levamisole, pyrantel or methyridine.

As already mentioned, the lactogenic substance and the anthelmintic agent may be administered successively or concurrently. For successive administration the preferred lactogenic substances, mentioned above, may be given parenterally or orally and they may may be used alone or in combination with pharmaceutically acceptable carriers, the proportions of which is determined by the solubility and chemical nature of the compound and chosen route of administration. As for the preferred anthelmintic agents they are best administered as a drench solution or suspension in a pharmaceutically acceptable vehicle, which is squirted down the throat of the animal with a drenching gun or in the manner generally used for each agent. For the concurrent administration of the preferred lactogenic substances and anthelmintic agents a similar oral route is best employed.

The dosages of the preferred lactogenic substances and anthelmintic agents may vary with the form of administration and the particular compound chosen. They also vary with the particular host under treatment. For successive administration, the preferred lactogenic substances may be given parenterally as sterile solutions in daily doses of 1 $\mu$g to 50 $\mu$g/kg of animal weight or orally in solid form or in solutions or suspensions in daily doses of 1 $\mu$g to 500 $\mu$g/kg of animal weight. The dose of the preferred anthelmintic agents is 10 mg to 750 mg/kg of animal weight or as directed by the manufacturer for each agent. Generally one oral dose is sufficient but if necessary doses may be given on consecutive days. For concurrent administration the preferred lactogenic substances and anthelmintic agents may be given as a drench suspension or solution in respective dosages of 1 $\mu$g to 500 $\mu$g/kg of animal weight for the lactogenic substances and 10 mg to 750 mg/kg for the anthelmintic agents.

Preferably when administered successively the anthelmintic agent is administered one to three weeks after the administration of the lactogenic substance or after the beginning of lactation.

The following example will illustrate the invention.

EXAMPLE

Twelve unbred ewes (8–9 months old), weighing approximately 40 kg each were chosen at random and were kept indoors in parasite-free pens. The pens were heated 24 hours a day and were artifically lit for approximately 18–20 hours a day. They were fed hay and concentrates throughout the experiment. The animals were practically nematode-free from birth. This was determined by fecal examination and necropsy examination of 7 other ewes chosen from the same flock. The animals were separated into two groups of six ewes each. A lactogenic substance, i.e. diethylstilbestrol, was administered to the animals of the first group (ewes No. 11, 12, 13, 15, 20 and 23) to induce lactation. The animals of the second group (ewes No. 37, 40, 44, 47, 409 and 737) were untreated and served as control.

Diethylstilbestrol in corn oil was administered daily by subcutaneous injection to the ewes of the first group in a dose of 0.25 mg/ml per ewe from November 18 to December 15 and thereafter in a dose of 0.1 mg/ml per ewe from December 16 to January 2. The administration of the lactogenic substance was stopped and the animals were hand-milked twice daily from January 3 to February 3. Lactation or the state of lactation was induced in all treated animals. Udder development and secretion started approximately 8 days after the first injection of diethylstilbestrol. "True" milk appeared 17 days later and milk production peaked around January 19.

On January 14 the animals of both groups were infected by the oral administration to each animal of 7000 third stage infective larvae of *Haemonchus contortus*, which were harvested by culturing infective faeces at room temperature for 7–10 days. On January 31, ewes No. 12, 13 and 23 of the first group (lactating) and 37, 40 and 737 of the second group (non-lactating) were given orally 31 g of phenothiazine using a drench gun. The animals of both groups were sacrificed on February 3. Abomasal contents and peptic digestion of the mucosa were examined for nematodes. Adult forms and inhibited or dormant larvae of *Haemonchus contortus* were differentiated and counted.

The results of the *Haemonchus contortus* counts are given in the following Table:

TABLE

*Haemonchus Contortus* Counts at Necropsy of Ewes

| EWE No. | TREATMENT | HAEMONCHUS CONTORTUS | | |
|---|---|---|---|---|
| | | ADULTS | LARVAE | TOTAL |
| 11 | Lactating (DES)* | 6040 | 350 | 6390 |
| 15 | Lactating (DES) | 3360 | 770 | 4130 |
| 20 | Lactating (DES) | 400 | 60 | 460 |
| MEAN | Lactating (DES) | 3266 | 393 | 3660 |
| 44 | Non-Lactating | 2000 | 680 | 2680 |
| 47 | Non-Lactating | 1370 | 2110 | 3480 |
| 409 | Non-Lactating | 100 | 810 | 920 |
| MEAN | Non-Lactating | 1156 | 1160 | 2322 |
| 12 | Lactating (DES) + Phenothiazine | 40 | 410 | 450 |
| 13 | Lactating (DES) + Phenothiazine | 100 | 270 | 370 |
| 23 | Lactating (DES) + Phenothiazine | 320 | 80 | 400 |
| MEAN | Lactating (DES) + Phenothiazine | 150 | 253 | 407 |
| 37 | Non-Lactating + Phenothiazine | 0 | 1990 | 1990 |
| 40 | Non-Lactating + Phenothiazine | 0 | 1530 | 1530 |
| 737 | Non-Lactating + Phenothiazine | 0 | 1620 | 1620 |
| MEAN | Non-Lactating + Phenothiazine | 0 | 1713 | 1713 |

*DES = diethylstilbestrol

It can be seen from the Table that the total nematode burdens before anthelmintic treatment were similar in the lactating (No. 11, 15 and 20) and non-lactating (No. 44, 47 and 409) ewes. However 90% of the *Haemonchus contortus* populations in the lactating group were found to be adult, while in the non-lactating group only 50% of the total nematode populations were adult, the remainder being dormant or inhibited in their development at the fourth larval stage. The anthelmintic treatment resulted in a 89% reduction of nematode burden in the lactating ewes (No. 12, 13 and 23) and only a 26% reduction in non-lactating ewes (No. 37, 40 and 737).

These results clearly demonstrate that the administration of a lactogenic substance prevents most of the infective larvae from becoming dormant or inhibited in their development at the fourth larval stage and allows these infective larvae to develop normally to the adult forms whereby the latter become susceptible to the action of an anthelmintic agent, since a 90% reduction in the total nematode populations is observed in ewes treated with diethylstilbestrol and phenothiazine and only a 26% reduction in the animals treated with phenothiazine alone. These results also confirm the observation by J. Armour, cited above, to the effect that anthelmintic agents are not effective against dormant or inhibited larvae.

Similarly the parenteral administration to ewes, infected in the fall or winter with third stage infective larvae of gastrointestinal nematodes, of diethylstilbestrol in a dose of 1 μg to 50 μg/kg of animal weight, followed by the treatment with phenothiazine, thiabendazole, cambendazole, mebendazole, tetramisole, levamisole, pyrantel or methyridine in doses ranging from 10 mg to 750 mg/kg or as directed by the manufacturer for each agent, produces the same effects.

Again similarly the oral administration to ewes, infected in the fall or winter with third stage infective larvae of gastrointestinal nematodes, of diethylstilbestrol in a dose of 1 μg to 500 μg/kg of animal weight, prior or concurrently to the treatment with phenothiazine, thiabendazole, cambendazole, mebendazole, tetramisole, levamisole, pyrantel or methylridine in doses ranging from 10 mg to 750 mg/kg of animal weight or as directed by the manufacturer for each agent, produces the same effect.

Again similarly the parenteral administration to ewes, infected in the fall or winter with third stage infective larvae of gastrointestinal nematodes, of estrone, estradiol, estradiol 3,17-diacylates, such as for example estradiol 3,17-dipropionate or estradiol 3,17-dibenzoate, ethynylestradiol or mestranol in doses ranging from 1 to μg to 50 μg/kg of animal weight, followed by the treatment with phenothiazine, thiabendazole, cambendazole, mebendazole, tetramisole, levamisole, pyrantel or methyridine in doses ranging from 10 mg to 750 mg/kg of animal weight or as directed by the manufacturer for each agent, produces the same results.

Again similarly the oral administration to ewes, infected in the fall or winter with third stage infective larvae of gastrointestinal nematodes, of estrone, estradiol, estradiol diacylates, such as for example estradiol 3,17-dipropionates or estradiol 3,17-dibenzoate, ethynylestradiol, or mestranol in doses ranging from 1 μg to 500 μg/kg of animal weight, prior or concurrently to the treatment with phenothiazine, thiabendazole, cambendazole, mebendazole, tetramisole, levamisole, pyrantel or methyridine in doses ranging from 10 mg to 750 mg/kg of animal weight or as directed by the manufacturer for each agent, produces the same results.

Again similarly the parenteral administration to cattle, infected in the fall or winter with third stage infective larvae of gastrointestinal nematodes, of diethylstilbestrol, estrone, estradiol, estradiol 3,17-diacylates, such as for example estradiol 3,17-dipropionate or estradiol 3,17-dibenzoate, ethynylestradiol or mestranol in doses ranging from 1 μg to 50 μg/kg of animal weight, followed by the treatment with phenothiazine, thiabendazole, cambendazole, mebendazole, tetramizole, levamisole, pyrantel or methylridine, in doses ranging from 10 mg to 750 mg/kg of animal weight or as directed by the manufacturer for each agent, produces the same effects.

Again similarly the oral administration to cattle, infected in the fall or winter by third stage infective larvae of gastrointestinal nematodes, of diethylstilbestrol, estrone, estradiol, estradiol 3,17-diacylates, such as for example estradiol 3,17-dipropionate or estradiol 3,17-dibenzoate, ethynylestradiol or mestranol in doses ranging from 1 μg to 500 μg/kg of animal weight, prior or concurrently to the treatment with phenothiazine, thiabendazole, cambendazole, mebendazole, tetramisole, levamisole, pyrantel or methylridine in doses ranging from 10 mg to 750 mg/kg of animal weight or as directed by the manufacturer for each agent, produces the same results.

I claim:

1. A method of treatment for the control of gastrointestinal nematode parasites in domestic animals infected with inhibited or inhibition-prone larvae of such parasites which comprises administering successively or concurrently from 1 microgram to 500 micrograms per kilogram of animal weight of a lactogenic substance and from 10 milligrams to 750 milligrams per kilogram of animal weight of an anthelmintic agent.

2. A method of treatment, as claimed in claim 1, for the control of gastrointestinal nematode parasites in domestic animals, which comprises administering prior to stabling time, successively or concurrently a lactogenic substance and an anthelmintic agent.

3. A method of treatment, as claimed in claim 2, for the control of gastrointestinal nematode parasites in sheep and cattle, which comprises administering prior to stabling time, successively or concurrently a lactogenic substance and an anthelmintic agent.

4. A method of treatment, as claimed in claim 3, for the control of gastrointestinal nematode parasites in sheep and cattle, which comprises administering, successively or concurrently, prior to stabling time, an estrogen and an anthelmintic agent.

5. A method of treatment, as claimed in claim 4 for the control of gastrointestinal nematode parasites in sheep and cattle which comprises administering successively or concurrently prior to stabling time, an estrogen selected from the group consisting of diethylstilbestrol, estrone, estradiol, estradiol diacylates, ethynylestradiol or mestranol, and an anthelmintic agent.

6. A therapeutic composition for the control of gastrointestinal nematode parasites in sheep and cattle, which comprises 1 μg to 500 μg/kg of animal weight of an estrogen and 10 mg to 750 mg/kg of animal weight of an anthelmintic agent, in the form of solutions or suspensions in pharmaceutically acceptable carriers.

7. A therapeutic composition as claimed in claim 6 for the control of gastrointestinal nematode parasites in sheep and cattle, which comprises 1 μg/kg to 500 μg/kg of animal weight of an estrogen selected from the group consisting of diethylstibestrol, estrone, estradiol, estradiol 3,17-diacylates, ethylnylestradiol and mestranol and 10 mg to 750 mg/kg of animal weight of an anthelmintic agent selected from the group, consisting of phenothiazine, thiabendazole, cambendazole, mebendazole, tetramisole, levamisole, pyrantel and methyridine, in the form of solutions or suspensions in pharmaceutically acceptable carriers.

* * * * *